(12) United States Patent
Morgen et al.

(10) Patent No.: US 9,084,727 B2
(45) Date of Patent: *Jul. 21, 2015

(54) METHODS AND COMPOSITIONS FOR MAINTAINING ACTIVE AGENTS IN INTRA-ARTICULAR SPACES

(75) Inventors: Michael M. Morgen, Bend, OR (US); Warren K. Miller, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,965

(22) Filed: May 10, 2012

(65) Prior Publication Data

US 2012/0289469 A1 Nov. 15, 2012

Related U.S. Application Data

(60) Provisional application No. 61/484,552, filed on May 10, 2011.

(51) Int. Cl.
| | |
|---|---|
| *C08B 37/02* | (2006.01) |
| *A61K 31/721* | (2006.01) |
| *A61K 9/16* | (2006.01) |
| *A61K 9/00* | (2006.01) |
| *A61K 31/4422* | (2006.01) |
| *C08L 5/02* | (2006.01) |

(52) U.S. Cl.
CPC ............ *A61K 9/1652* (2013.01); *A61K 9/0075* (2013.01); *A61K 31/4422* (2013.01); *C08B 37/0021* (2013.01); *C08L 5/02* (2013.01)

(58) Field of Classification Search
CPC ............ A61K 9/0075; A61K 9/1652; A61K 31/4422; C08L 5/02; C08L 37/0021
USPC ..................................... 536/51, 112; 514/59
See application file for complete search history.

(56) References Cited

U.S. PATENT DOCUMENTS

| | | | |
|---|---|---|---|
| 4,451,452 A | 5/1984 | Deibig et al. | |
| 4,501,726 A | 2/1985 | Schröder et al. | |
| 4,615,881 A | 10/1986 | Deibig et al. | |
| 4,713,249 A | 12/1987 | Schröder | |
| 5,624,666 A * | 4/1997 | Coffindaffer et al. | 424/70.21 |
| 5,688,931 A | 11/1997 | Nogusa et al. | |
| 5,744,153 A | 4/1998 | Yewey et al. | |
| 5,759,563 A | 6/1998 | Yewey et al. | |
| 5,780,044 A | 7/1998 | Yewey et al. | |
| 5,792,475 A | 8/1998 | Davis et al. | |
| 5,928,669 A | 7/1999 | Davis et al. | |
| 5,981,719 A | 11/1999 | Woiszwillo et al. | |
| 6,048,515 A | 4/2000 | Kresse et al. | |
| 6,090,925 A | 7/2000 | Woiszwillo et al. | |
| 6,165,506 A | 12/2000 | Jain et al. | |
| RE37,053 E | 2/2001 | Hanes et al. | |
| 6,200,590 B1 | 3/2001 | Eley | |
| 6,268,053 B1 | 7/2001 | Woiszwillo et al. | |
| 6,303,148 B1 | 10/2001 | Hennink et al. | |
| 6,395,302 B1 | 5/2002 | Hennink et al. | |
| 6,497,903 B1 | 12/2002 | Hennink et al. | |
| 6,541,039 B1 | 4/2003 | Lesniak et al. | |
| 6,576,221 B1 | 6/2003 | Kresse et al. | |
| 6,589,557 B2 | 7/2003 | Straub et al. | |
| 6,589,562 B1 | 7/2003 | Shefer et al. | |
| 6,610,317 B2 | 8/2003 | Straub et al. | |
| 6,632,671 B2 | 10/2003 | Unger | |
| 6,685,927 B2 | 2/2004 | Sumian et al. | |
| 6,740,631 B2 | 5/2004 | Shefer et al. | |
| 6,800,297 B2 | 10/2004 | Altreuter et al. | |
| 6,825,161 B2 | 11/2004 | Shefer et al. | |
| 6,835,389 B1 | 12/2004 | Dohi et al. | |
| 6,887,493 B2 | 5/2005 | Shefer et al. | |
| 6,932,983 B1 | 8/2005 | Straub et al. | |
| 6,979,466 B2 | 12/2005 | Lesniak et al. | |
| 6,998,393 B2 | 2/2006 | Jin et al. | |
| 7,060,296 B2 | 6/2006 | Hennink et al. | |
| 7,087,246 B2 | 8/2006 | Kim et al. | |
| 7,163,700 B2 | 1/2007 | Bogue | |
| 7,300,919 B2 | 11/2007 | Patton | |
| 7,378,110 B2 | 5/2008 | Truong Le et al. | |
| 7,468,151 B2 | 12/2008 | van Buitenen et al. | |
| 7,521,069 B2 | 4/2009 | Patton et al. | |

(Continued)

FOREIGN PATENT DOCUMENTS

| | | |
|---|---|---|
| DE | 4136324 | 5/1993 |
| DE | 4208946 | 9/1993 |

(Continued)

OTHER PUBLICATIONS

Ahlers et al.; DE 4136324; May 13, 1993 (English Machine Translation).*

(Continued)

*Primary Examiner* — Shaojia Anna Jiang
*Assistant Examiner* — Michael C Henry
(74) *Attorney, Agent, or Firm* — Klarquist Sparkman, LLP

(57) ABSTRACT

Methods and compositions for maintaining an active agent in an intra-articular space are disclosed. Methods of delivering the compositions to an intra-articular space and methods of making the compositions also are disclosed. The compositions comprise an active agent and a polymer comprising at least one cationic group. A fluid including the composition may be injected into an intra-articular space in a human or animal whereby the composition associates with endogenous material in the intra-articular space. In some embodiments, the fluid further comprises a poorly aqueous soluble polymer.

24 Claims, 1 Drawing Sheet

(56) References Cited

U.S. PATENT DOCUMENTS

| | | | |
|---|---|---|---|
| 7,541,022 B2 | 6/2009 | Staniforth et al. | |
| 7,625,865 B2 | 12/2009 | Colombo et al. | |
| 7,928,089 B2 | 4/2011 | Morton et al. | |
| 2002/0076443 A1 | 6/2002 | Stein et al. | |
| 2002/0141943 A1 | 10/2002 | Kresse et al. | |
| 2003/0026843 A1 | 2/2003 | Bogue | |
| 2003/0118514 A1 | 6/2003 | Larhrib et al. | |
| 2003/0207776 A1 | 11/2003 | Shefer et al. | |
| 2004/0062778 A1 | 4/2004 | Shefer et al. | |
| 2004/0091535 A1 | 5/2004 | Vachon et al. | |
| 2004/0105821 A1 | 6/2004 | Bernstein et al. | |
| 2004/0109894 A1 | 6/2004 | Shefer et al. | |
| 2004/0137071 A1 | 7/2004 | Unger | |
| 2004/0176391 A1 | 9/2004 | Weers et al. | |
| 2004/0184995 A1 | 9/2004 | Katsuma et al. | |
| 2004/0224019 A1 | 11/2004 | Shefer et al. | |
| 2005/0058710 A1 | 3/2005 | Straub et al. | |
| 2005/0065047 A1 | 3/2005 | Shefer et al. | |
| 2005/0112235 A1 | 5/2005 | Shefer et al. | |
| 2005/0181059 A1 | 8/2005 | Jacob et al. | |
| 2005/0191246 A1 | 9/2005 | Bechtold-Peters et al. | |
| 2005/0238716 A1 | 10/2005 | Verrijk et al. | |
| 2005/0250881 A1 | 11/2005 | Gref et al. | |
| 2005/0271728 A1* | 12/2005 | Nomura et al. | 424/487 |
| 2006/0025355 A1 | 2/2006 | Duddu et al. | |
| 2006/0039985 A1 | 2/2006 | Bennett et al. | |
| 2006/0110462 A1 | 5/2006 | Papadopoulos et al. | |
| 2006/0121121 A1 | 6/2006 | Jin et al. | |
| 2006/0127480 A1 | 6/2006 | Tobyn et al. | |
| 2006/0141029 A1 | 6/2006 | Heller et al. | |
| 2006/0141047 A1 | 6/2006 | Heller et al. | |
| 2006/0141075 A1 | 6/2006 | Talbott | |
| 2006/0204582 A1 | 9/2006 | Stein et al. | |
| 2006/0246142 A1 | 11/2006 | Liversidge et al. | |
| 2007/0003615 A1 | 1/2007 | Jenkins et al. | |
| 2007/0003628 A1 | 1/2007 | Liversidge et al. | |
| 2007/0015719 A1 | 1/2007 | Jenkins et al. | |
| 2007/0031490 A1 | 2/2007 | Loebenberg et al. | |
| 2007/0042049 A1 | 2/2007 | Liversidge et al. | |
| 2007/0104792 A1 | 5/2007 | Jenkins | |
| 2007/0134339 A1 | 6/2007 | Jenkins et al. | |
| 2007/0134341 A1 | 6/2007 | Kipp et al. | |
| 2007/0148100 A1 | 6/2007 | Jenkins | |
| 2007/0148236 A1 | 6/2007 | Babcock et al. | |
| 2007/0178051 A1 | 8/2007 | Pruitt et al. | |
| 2007/0178152 A1 | 8/2007 | Shelton et al. | |
| 2008/0057003 A1 | 3/2008 | Bechtold-Peters et al. | |
| 2008/0152585 A1 | 6/2008 | Ryde et al. | |
| 2008/0213374 A1 | 9/2008 | Carty et al. | |
| 2008/0220074 A1 | 9/2008 | Bosch et al. | |
| 2008/0234227 A1 | 9/2008 | Soula et al. | |
| 2008/0241267 A1 | 10/2008 | Verrijk | |
| 2008/0292707 A1 | 11/2008 | Babcock et al. | |
| 2009/0047336 A1 | 2/2009 | Yang et al. | |
| 2009/0104277 A1* | 4/2009 | Kristensen et al. | 424/501 |
| 2009/0181100 A1 | 7/2009 | Bosch et al. | |
| 2009/0238867 A1 | 9/2009 | Jenkins et al. | |
| 2009/0269396 A1 | 10/2009 | Cipolla et al. | |
| 2009/0274765 A1 | 11/2009 | Beduneau et al. | |
| 2010/0081956 A1 | 4/2010 | Hyde et al. | |
| 2012/0003282 A1 | 1/2012 | Miller et al. | |

FOREIGN PATENT DOCUMENTS

| | | |
|---|---|---|
| EP | 0051707 | 5/1982 |
| EP | 0053580 | 6/1982 |
| EP | 0842657 | 5/1998 |
| EP | 0914832 | 5/1999 |
| EP | 1184032 | 3/2002 |
| EP | 1371364 | 12/2003 |
| EP | 1393718 | 3/2004 |
| EP | 1741424 | 1/2007 |
| WO | WO94/02122 | 2/1994 |
| WO | WO96/04017 | 2/1996 |
| WO | WO98/00170 | 1/1998 |
| WO | WO98/22093 | 5/1998 |
| WO | WO98/31346 | 7/1998 |
| WO | WO98/58673 | 12/1998 |
| WO | WO00/13672 | 3/2000 |
| WO | WO00/72827 | 12/2000 |
| WO | WO01/60339 | 8/2001 |
| WO | WO01/95877 | 12/2001 |
| WO | WO01/97865 | 12/2001 |
| WO | WO02/00207 | 1/2002 |
| WO | WO02/17884 | 3/2002 |
| WO | WO02/38126 | 5/2002 |
| WO | WO02/45575 | 6/2002 |
| WO | WO02/083154 | 10/2002 |
| WO | WO03/030872 | 4/2003 |
| WO | WO03/092659 | 11/2003 |
| WO | WO03/105780 | 12/2003 |
| WO | WO2004/006897 | 1/2004 |
| WO | WO2004/012690 | 2/2004 |
| WO | WO2004/019908 | 3/2004 |
| WO | WO2004/030659 | 4/2004 |
| WO | WO2004/041991 | 5/2004 |
| WO | WO2004/082660 | 9/2004 |
| WO | WO2004/112695 | 12/2004 |
| WO | WO2004/112696 | 12/2004 |
| WO | WO2005/007080 | 1/2005 |
| WO | WO2005/032511 | 4/2005 |
| WO | WO2005/055976 | 6/2005 |
| WO | WO2005/084644 | 9/2005 |
| WO | WO2005/115330 | 12/2005 |
| WO | WO2006/002140 | 1/2006 |
| WO | WO2006/003504 | 1/2006 |
| WO | WO2006/036617 | 4/2006 |
| WO | WO2006/130943 | 12/2006 |
| WO | WO2007/064912 | 6/2007 |
| WO | WO2007/146943 | 12/2007 |
| WO | WO2008/038111 | 4/2008 |
| WO | WO2008/070538 | 6/2008 |
| WO | WO2008/092057 | 7/2008 |
| WO | WO2008/137960 | 11/2008 |
| WO | WO2008/151022 | 12/2008 |
| WO | WO2009/046440 | 4/2009 |
| WO | WO2010/009146 | 1/2010 |
| WO | WO2010/102065 | 9/2010 |
| WO | WO2010/102066 | 9/2010 |
| WO | WO2010/132827 | 11/2010 |
| WO | WO2010/146406 | 12/2010 |
| WO | WO2010/146408 | 12/2010 |
| WO | WO2010/146409 | 12/2010 |
| WO | WO 2011/057017 | 5/2011 |
| WO | WO 2011/060250 | 5/2011 |

OTHER PUBLICATIONS

Cruz, et al.,, "Peptide Synthesis Containing a B-Cell and a T-Cell Epitope on Dextran Beads and Evaluation of Humoral Response Against Bead-Peptide Construct," *Letters in Peptide Science*, 7: 229-237, 2000.

Curatolo, et al. "Utility of Hydroxypropylmethylcellulose Acetate Succinate (HPMCAS_for Initiation and Maintenance of Drug Supersaturation in the GI Milieu," Pharmaceutical Research 26:6, pp. 1419-1431 (Jun. 2009).

Heinze et al., "Functional Polymers Based on Dextran," *Advances in Polymer Science*, vol. 205, pp. 199-291 (Sep. 2006).

International Search Report and Written Opinion dated Jun. 11, 2010 (mailed Jun. 17, 2010), issued in International Application No. PCT/US2010/026127.

International Search Report and Written Opinion, dated Jan. 28, 2011 (mailed Feb. 22, 2011), issued in International Application No. PCT/US2010/056515.

International Search Report and Written Opinion dated Nov. 28, 2011 (mailed Dec. 6, 2011), issued in International Application No. PCT/US2011/040222.

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, pp. 1748-1752 (Nov. 1998).

(56) References Cited

OTHER PUBLICATIONS

Lemarchand et al., "Influence of polysaccharide coating on the interactions of nanoparticles with biological systems," *Biomaterials*, vol. 27, Issue 1, pp. 108-118 (Jan. 2006).

Liebert et al., "Nanoparticles on the Basis of Highly Functionalized Dextrans," *Journal of the American Chemical Society*, vol. 127, No. 30, pp. 10484-10485 (Aug. 2005).

Niwa et al., "Aerosolization of Lactide/Glycolide Copolymer (PLGA) Nanospheres for Pulmonary Delivery of Peptide-drugs," *Yakugaku Zasshi Journal of the Pharmaceutical Society of Japan*, vol. 115, No. 9, pp. 732-741 (Sep. 1995).

Prado et al., "Preparation and characterization of a novel starch-based interpolyelectrolyte complex as matrix for controlled drug release," *Carbohydrate Research*, vol. 344, No. 11, pp. 1325-1331 (Jul. 2009).

Rasenack et al., "Micronization of Anti-Inflammatory Drugs for Pulmonary Delivery by a Controlled Crystallization Process," *Journal of Pharmaceutical Sciences*, vol. 92, No. 1, pp. 35-44 (Jan. 2003).

Sham et al., "Formulation and characterization of spray-dried powders containing nanoparticles for aerosol delivery to the lung," *International Journal of Pharmaceutics*, vol. 269, Issue 2, pp. 457-467 (Jan. 2004).

Steckel et al., "In-situ-micronization of disodium cromoglycate for pulmonary delivery," *European Journal of Pharmaceutics and Biopharmaceutics*, vol. 55, No. 2, pp. 173-180 (Mar. 2003).

Steckel et al., "In vitro characterization of jet-milled and in-situ-micronized fluticasone-17-propionate," *International Journal of Pharmaceutics*, vol. 258, Issues 1-2, pp. 65-75 (Jun. 2003).

Yamamoto et al., "Poly(lactic-co-glycolic acid) Nanosphere Composite Prepared with Mechanofusion Dry Powder Composition System for Improving Pulmonary Insulin Delivery with Dry Powder Inhalation," *Journal of Pharmaceutical Science and Technology, Japan*, vol. 64, No. 4, pp. 245-253 (Jan. 2004).

US 5,849,884, 12/1998, Woiszwillo et al. (withdrawn)

\* cited by examiner

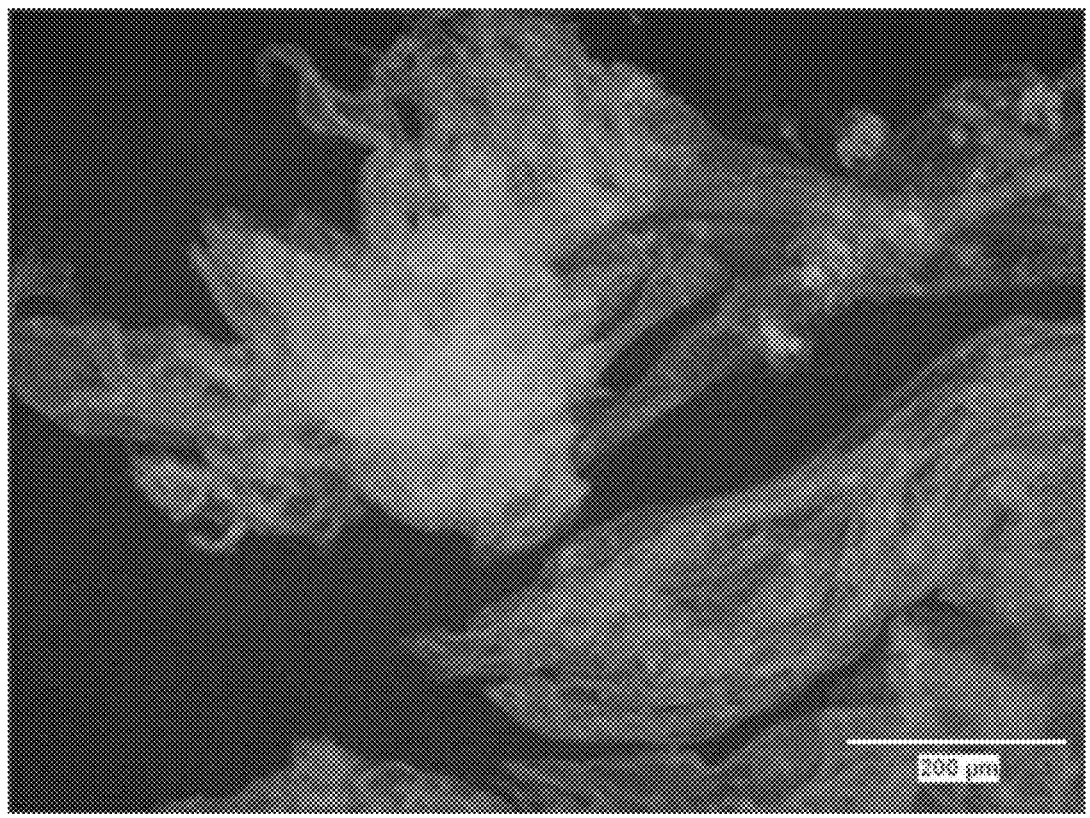

METHODS AND COMPOSITIONS FOR MAINTAINING ACTIVE AGENTS IN INTRA-ARTICULAR SPACES

CROSS REFERENCE TO RELATED APPLICATION

The present application claims priority to and the benefit of U.S. Provisional Patent Application No. 61/484,552, filed May 10, 2011, which is incorporated herein in its entirety by reference.

TECHNICAL FIELD

Methods and compositions for maintaining an active agent in an intra-articular space are disclosed. The compositions comprise an active agent and a polymer comprising at least one cationic group. A fluid including the composition may be injected into an intra-articular space in a human or animal whereby the composition associates with endogenous material in the intra-articular space.

BACKGROUND

Pharmaceutically active agents are generally formulated as solid or liquid dosage forms for administration. Such dosage forms generally comprise the active agent combined with excipients to form materials that may be conveniently and reliably administered to a patient in need of such therapy, and following administration, the active agent is absorbed and distributed in the patient in a way that leads to good efficacy and safety.

SUMMARY

Embodiments of compositions and methods for maintaining an active agent in an intra-articular space are disclosed. Embodiments of methods for delivering the compositions to the intra-articular space and methods of making the compositions also are disclosed.

In one embodiment, a method for maintaining an active agent in an intra-articular space includes providing a composition comprising an active agent and a polymer comprising at least one cationic group, and admixing the composition with a liquid to form a fluid, thereby forming a mixture capable of associating with endogenous material in the intra-articular space. In one embodiment, a method for delivering an active agent to an intra-articular space includes providing a fluid comprising (a) an active agent, (b) a polymer comprising at least one cationic group, and (c) a liquid, wherein after administration of said fluid to an in vitro synovial fluid, at least one of said active agent and said polymer comprising at least one cationic group is associated with at least one component of said synovial fluid. In one embodiment, a method for delivering an active agent to an intra-articular space includes injecting the fluid into an intra-articular space in a human or animal, wherein, following injection, at least one of the active agent and polymer is associated with endogenous material in the intra-articular space.

In one embodiment, the fluid further includes a poorly aqueous soluble polymer. In one embodiment, the fluid includes a liquid selected from water, water for injection, isotonic saline, hypertonic saline, and Lactated Ringer's solution.

In one embodiment, the fluid is a solution in which the active agent and the polymer comprising at least one cationic group are dissolved. In another embodiment, the fluid is a suspension of particles. In yet another embodiment, the suspended particles are nanoparticles.

In one embodiment, the active agent is joined with the polymer comprising at least one cationic group. In another embodiment, the fluid further includes a poorly aqueous soluble polymer, and the active agent is joined with the poorly aqueous soluble polymer.

In one embodiment, the polymer comprising at least one cationic group is selected from chitosan, polyethyleneimine, polylysine, amino polyethylene glycol, diethylaminoethyl dextran, ammonio acrylate polymers, ammonio methacrylate polymers, ammonio acrylate and methacrylate copolymers, poly(ethylacrylate-co-methyl methacrylate-co-trimethylammonioethyl methacrylate chloride), and cationic dextran polymer derivatives comprising an ester-linked amine-containing substituent, selected from

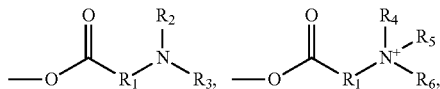

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of the ester-linked amine-containing substituent is at least 0.03.

In another embodiment, the polymer comprising at least one cationic group is a cationic dextran polymer derivative comprising (a) an ester-linked amine-containing substituent, selected from

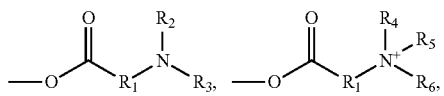

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03; and (b) an alkyl ester substituent selected from acetate, propionate, butyrate, isobutyrate, and mixtures thereof, wherein the degree of substitution of said alkyl ester substituent is at least 0.05.

In one embodiment, the poorly aqueous soluble polymer is selected from ethylcellulose, cellulose acetate, cellulose propionate, cellulose butyrate, cellulose acetate butyrate, and hydrophobic dextran polymer derivatives, and mixtures thereof. In another embodiment, the poorly aqueous soluble polymer is a hydrophobic dextran polymer derivative comprising an alkyl ester substituent selected from acetate, propionate, butyrate, isobutyrate, and mixtures thereof, wherein the degree of substitution of the alkyl ester substituent is at least 0.05.

In one embodiment, a composition includes a dry powder comprising an active agent and a polymer comprising at least one cationic group, wherein the dry powder, when admixed with a liquid and injected into an intra-articular space, is capable of maintaining the active agent in the intra-articular space by associating with endogenous material in the intra-articular space. In another embodiment the composition, when admixed with a liquid and injected into an intra-articular space, is capable of maintaining the active agent in the intra-articular space by forming an intermolecular interaction with endogenous material in the intra-articular space. In one embodiment, after administration to an in vitro synovial fluid, at least one of the active agent and the polymer is associated with at least one component of the synovial fluid.

In one embodiment, the dry powder is reconstituted with a liquid to form a fluid suitable for injecting into an intra-articular space of a human or animal, wherein, after reconstitution, at least one of the active agent and the polymer is associated with endogenous material in the intra-articular space. In one embodiment, the fluid is a solution of the active agent and the polymer comprising at least one cationic group. In another embodiment, the fluid is a suspension of the active agent and the polymer comprising at least one cationic group In one embodiment, the polymer comprising at least one cationic group is a cationic dextran polymer derivative comprising a) an ester-linked amine-containing substituent, selected from

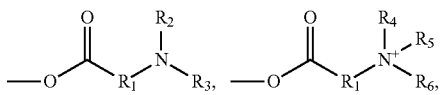

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03; and (b) an alkyl ester substituent selected from acetate, propionate, butyrate, isobutyrate, and mixtures thereof, wherein the degree of substitution of said alkyl ester substituent is at least 0.05.

In one embodiment, the composition further includes a poorly aqueous soluble polymer. In one embodiment, the poorly aqueous soluble polymer is a hydrophobic dextran polymer derivative comprising an alkyl ester substituent selected from acetate, propionate, butyrate, isobutyrate, and mixtures thereof, wherein the degree of substitution of the alkyl ester substituent is at least 0.05

In another embodiment disclosed is a method for maintaining an active agent in an intra-articular space comprising (a) providing a composition comprising an active agent and a polymer having at least one cationic group, and (b) admixing the composition with a liquid thereby forming a mixture capable of maintaining the active agent in the intra-articular space by associating with endogenous material therein when injected into the intra-articular space such that the active agent is retained therein for a longer time than when the active agent is administered to the intra-articular space in the absence of the polymer.

BRIEF DESCRIPTION OF THE DRAWINGS

FIG. 1 is a fluorescent microscopic image of dextran-based cationic nanoparticles associated with hyaluronic acid.

DETAILED DESCRIPTION

The present disclosure relates to a method of delivering an active agent to an intra-articular space. The method comprises providing a fluid comprising (i) an active agent, and (ii) a polymer comprising at least one cationic group. The fluid is injected into an intra-articular space in a human or animal such that the active agent and polymer are associated with endogenous material in the intra-articular space. Embodiments of the compositions and methods for making them are described in detail below.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited. The compositions described herein can be used for a wide variety of applications. In one embodiment, the compositions are intended for delivery of active agents to intra-articular spaces. As used herein, "intra-articular spaces" means delivery to joints, including the knee, elbow, wrist, ankle, or other joints. When delivered to intra-articular spaces, certain embodiments of the composition comprising an active agent and a polymer comprising at least one cationic group become associated with endogenous materials present in the synovial fluid. As used herein, the term "associated with" means there is an intermolecular interaction between at least one component of the composition and at least one endogenous material present in the synovial fluid. Intermolecular interactions may include, but are not limited to, ionic crosslinking, hydrophobic interactions, and/or van der Waals interactions. In one embodiment, the composition interacts with endogenous hyaluronate to form ionically crosslinked hydrogels. In another embodiment, the composition further comprises a poorly aqueous soluble polymer that forms intermolecular interactions with endogenous material present in the synovial fluid. This leads to increased retention of the active agent in the joint, and a slow release of the active agent, providing an extended therapeutic window, and requiring less frequent injections, as compared with currently available compositions such as compositions that do not contain polymers comprising at least one cationic group.

In one embodiment, the disclosure described herein relates to a delivery fluid that comprises a solution comprising an active agent and a polymer comprising at least one cationic group. In another embodiment, the disclosure described herein relates to a delivery fluid that comprises an active agent and a polymer comprising at least one cationic group, wherein the delivery fluid is in the form of a suspension. In one embodiment, the delivery fluid further comprises a poorly aqueous soluble polymer. In one embodiment, a portion or all of the active agent may be in suspension, a portion or all of the polymer comprising at least one cationic group may be in suspension, or a portion of the active agent and a portion of the polymer comprising at least one cationic group may be in suspension.

In another embodiment, the disclosure described herein relates to a dry powder comprising an active agent and a polymer comprising at least one cationic group that may be reconstituted into a delivery fluid that may be administered intra-articularly.

Active Agents

In one embodiment, the disclosed methods and compositions are suitable for use with any biologically active compound desired to be administered to a patient (human or animal) in need of the active agent. The compositions may contain one or more active agents. As used herein, by "active agent" is meant a drug, medicament, pharmaceutical, therapeutic agent, nutraceutical, or other compound that may be desired to be administered to the body. The active agent may be a "small molecule," generally having a molecular weight of 2000 Daltons or less. The active agent may also be a "biological active agent." Biological active agents include proteins, antibodies, antibody fragments, antigens, peptides, oligonucleotides, vaccines, and various derivatives of such materials. In one embodiment, the active agent is a biological active agent selected from proteins, antibodies, antibody fragments, antigens, peptides, oligonucleotides, vaccines, and mixtures and derivatives thereof. In one embodiment, the active agent is a small molecule. In another embodiment, the active agent is a biological active agent. In one embodiment, the active agent is selected from a small molecule, a biological active agent, and mixtures thereof. In still another embodiment, the active agent is a mixture of a small molecule and a biological active agent.

The active agent may be highly water soluble (i.e., greater than 100 mg/mL at 25° C.), sparingly water soluble (i.e., 5-30 mg/mL), or poorly water soluble (i.e., less than 5 mg/mL). In one embodiment, the active agent is "poorly water soluble," and the active agent has a solubility in water (at 25° C.) of less than 5 mg/mL. The active agent may have an even lower water solubility, such as less than 1 mg/mL, less than 0.1 mg/mL, and even less than 0.01 mg/mL.

The active agent should be understood to include the non-ionized form of the active agent, pharmaceutically acceptable salts of the active agent, or any other pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and pro-drugs.

Examples of classes of active agents include, but are not limited to, compounds for use in the following therapeutic areas: anti-inflammatories, antibiotics, autoimmune disorder agents, antiviral agents, anticlotting agents, antibacterial and antifungal agents, steroids, corticosteroids, glucocorticoids, mineralocorticoids, caspase inhibitors, aggrecanase inhibitors, matrix metalloproteinases (MMP) inhibitors, nonsteroidal anti-inflammatory agents/analgesics (also known as NSAIDs), disease-modifying anti-rheumatic drugs (DMARDs), disease-modifying osteoarthritis drugs (DMOADs), cyclooxygenase 2 inhibitors (COX-2 inhibitors), analgesics, and mixtures thereof.

In certain embodiments, the active agent is joined with at least one of the polymers present in the composition, such as the polymer containing at least one cationic group and/or a poorly aqueous soluble polymer, such that following administration to the intra-articular space, the active agent is retained therein for a longer time than when the active agent is administered to the intra-articular space in the absence of the polymers. As used herein, the term "joined with" means the active agent is attached covalently or non-covalently to at least one of the polymers present in the composition.

In one embodiment, the active agent is joined to at least one of the polymers present in the composition via a covalent linkage. In another embodiment, the active agent is joined to at least one of the polymers present in the composition using a physiologically labile covalent linkage. By "physiologically labile covalent linkage" is meant a covalent bond that will release the active agent at the desired rate when introduced into an in vivo use environment. In one embodiment, the covalent bond has a half-life of 0.5 to 500 days. Exemplary physiologically labile covalent linkages include esters, ortho esters, ketals, acetals, disulfides, carbonates, phosphates, and phospho-esters. In one embodiment, the physiologically labile covalent linkage is an ester linkage.

In one embodiment, the active agent is joined to at least one of the polymers present in the composition via a non-covalent attachment. Examples of non-covalent attachment include ionic bonds, hydrogen bonds, van der Waals forces, hydrophobic interactions, or molecular entanglement. In one embodiment, the active agent is entrapped or entangled with at least one of the polymers present in the composition. This embodiment is useful when the active agent is a biological active agent. In one embodiment, the active agent is joined to at least one of the polymers through ionic forces. In one embodiment, the active agent is joined to at least one of the polymers through hydrogen bonds. In one embodiment, the active is joined to at least one of the polymers through van der Waals forces. In one embodiment, the active is joined to at least one of the polymers through hydrophobic interactions.

Polymers Comprising at Least One Cationic Group

The compositions comprise a polymer comprising at least one cationic group. In one embodiment, the polymer comprises more than one cationic group. In one embodiment, the polymers are biocompatible as described herein below. In another embodiment, the polymers are biodegradable as described herein below. In one embodiment, polymers comprising at least one cationic group include chitosan, polyethyleneimine, polylysine, amino polyethylene glycol, diethylaminoethyl dextran, ammonio acrylate polymers, ammonio methacrylate polymers, ammonio acrylate and methacrylate copolymers, poly(ethylacrylate-co-methyl methacrylate-co-trimethylammonioethyl methacrylate chloride), and cationic dextran polymer derivatives comprising an ester-linked amine-containing substituent, selected from

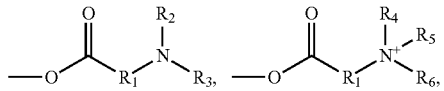

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl, groups, and $R_4$, $R_5$, and $R_6$ may be the same or different and are selected from methyl and ethyl groups.

In one embodiment, the polymer comprising at least one cationic group is characterized by a dissociation constant, known as the pKa. If the pH of a solution containing the polymer comprising at least one cationic group is the same as the pKa value, then 50 mol % of the cationic groups are ionized, and 50 mol % are non-ionized. As the pH decreases, a greater fraction of the cationic groups become ionized; as the pH increases, a greater fraction of the cationic groups become non-ionized.

In another embodiment, polymers comprising at least one cationic group include chitosan, polylysine, amino polyethylene glycol, diethylaminoethyl dextran, and cationic dextran polymer derivatives comprising an ester-linked amine-containing substituent, selected from

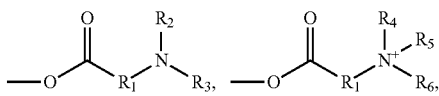

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups.

In yet another embodiment, polymers comprising at least one cationic group include diethylaminoethyl dextran, and cationic dextran polymer derivatives comprising an ester-linked amine-containing substituent, selected from

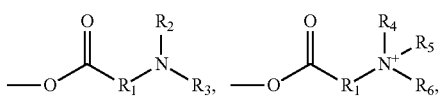

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups.

In still another embodiment, polymers comprising at least one cationic group include cationic dextran polymer derivatives comprising an ester-linked amine-containing substituent, selected from

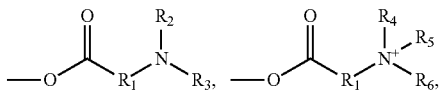

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups. Methods of making such polymers are discussed below.

The degree of substitution of the ester-linked amine-containing substituent is at least 0.03. As used herein, the term "degree of substitution" refers to the average number of substituents attached to one repeat unit, or monomer, of the dextran backbone; the maximum number of ester-linked amine-containing substituents that can be attached to a dextran backbone monomer is 3.0. In another embodiment, the degree of substitution of the ester-linked amine-containing substituents is at least 0.05. In other embodiments, higher degrees of substitution are desired. Thus, the degree of substitution of the ester-linked amine-containing substituents may be at least 0.10, at least 0.15, at least 0.2, or even higher.

In another embodiment, the degree of substitution of the ester-linked amine-containing substituents ranges from 0.03 to 2.95. In yet another embodiment, the degree of substitution of the ester-linked amine-containing substituents ranges from 0.05 to 2.95. Other degrees of substitution of the ester-linked amine-containing substituents may be beneficial, including from 0.05 to 2.95, from 0.1 to 2.5, from 0.15 to 2.0, and even from 0.2 to 2.0.

In one embodiment, the cationic dextran polymer derivative further comprises an alkyl ester substituent selected from acetate, propionate, butyrate, isobutyrate, and mixtures thereof. In another embodiment, the alkyl ester substituent is selected from acetate and propionate. In yet another embodiment, the alkyl ester substituent is acetate. In another embodiment, the alkyl ester substituent is propionate.

In one embodiment, the degree of substitution of the alkyl ester substituent is at least 0.05. In another embodiment, the degree of substitution of the alkyl ester substituent is at least 0.1. In still another embodiment, the degree of substitution of the alkyl ester substituent is at least 0.5. In yet another embodiment, the degree of substitution of the alkyl ester substituent is at least 1.0. In another embodiment, the degree of substitution of the alkyl ester substituent ranges from 0.05 to 2.95. In another embodiment, the degree of substitution of the alkyl ester substituent ranges from 0.1 to 2.5.

In one embodiment, the polymer comprising at least one cationic group is biocompatible. By "biocompatible" is meant that for one or more delivery routes, the polymer is compatible with and has no significant toxic effect on the living organism to which it is administered. In one embodiment, the polymer does not significantly elicit humoral or cell-based immune responses when administered in vivo.

In yet another embodiment, the polymer comprising at least one cationic group is biodegradable. By "biodegradable" is meant that the polymer will degrade when administered in vivo. By "degrade" is meant that in an in vivo use environment, the polymer is broken down into smaller species that can be absorbed, metabolized, and/or otherwise eliminated or "cleared" from the use environment within a time period of several days to several weeks or even several months. This degradation can occur through enzymatic, hydrolytic, oxidative, or other reactions or processes, as are well known in the art. The polymer may also degrade into aqueous soluble species that can be cleared from the in vivo use environment. For example, the degradation products may be renally cleared through the kidneys or may enter the lymphatic system and then exit through the gastro-intestinal tract.

Synthesis of Cationic Dextran Polymer Derivatives

Cationic dextran polymer derivatives may be synthesized using procedures known in the art. In one embodiment, an ester-linked amine-containing substituent is attached to a dextran polymer. In another embodiment, the ester-linked amine-containing substituent is first attached to the dextran polymer, and then an alkyl ester substituent is attached. In another embodiment, an alkyl ester substituent is first attached to the dextran polymer and then the ester-linked amine-containing substituent is attached to the dextran polymer. In still another embodiment, the ester-linked amine-containing substituent and an alkyl ester substituent are simultaneously attached to the dextran polymer.

In one embodiment, the cationic dextran polymer derivatives are synthesized using a homogeneous reaction by first dissolving the dextran polymer in a suitable solvent. Suitable solvents include, but are not limited to, dimethylformamide (DMF), dimethylacetamide (DMAC), formamide, dimethylsulfoxide (DMSO), methylene chloride, and mixtures thereof. Reactants and any catalysts and/or co-reactants are added to the reaction mixture, and the mixture is allowed to react at an appropriate temperature and for an appropriate time to achieve the desired degree of substitution. The reaction mixture may then be quenched, and the derivatized polymer precipitated and washed. The derivatized polymer may be purified prior to use or prior to further reaction. One skilled in the art will understand that standard polymer derivatization techniques may be applied to the synthesis of cationic dextran polymer derivatives. See for example *Advances in Polymer*

Science, 205, *Polysaccharides II*, edited by Dieter Klemm (Springer-Verlag, Berlin Heidelberg, 2006). The specific reaction conditions used to attach the ester-linked amine-containing substituents and alkyl ester substituents will vary depending on the properties of the substituent. In addition, for some reactants, protecting groups may be added to the reactants, and after performing the reaction, the protecting groups may be removed to form the desired substituent.

When amine-containing substituents are ester linked to dextran, activation of the carboxylic acid and/or the use of coupling agents is often utilized to increase the rate of reaction and improve yield. Activation or coupling agents such as N,N'-carbonyldiimidazole (CD) and N,N'-dicyclohexylcarbodiimide (DCC) may be employed using techniques known in the art. Similar reactions can be obtained using amine-containing substituents based on carboxylic acid chlorides and anhydrides. Such reactions often utilize the presence of a base to catalyze the reaction. See for example, T. Heinze, et al., *Advances in Polymer Science*, Vol. 205, pp. 199-291, 2006. A similar reaction scheme can be used to attach alkyl ester substituents to the dextran polymer.

Poorly Aqueous Soluble Polymer

In some embodiments, the disclosed compositions further comprise a poorly aqueous soluble polymer. By "poorly aqueous soluble" is meant that the polymer has a solubility of less than 0.1 mg/mL when administered alone at a concentration of 0.2 mg/mL to a phosphate-buffered saline solution (PBS) at pH 6.5 and ambient temperature.

In one embodiment, the poorly aqueous soluble polymer is selected from ethylcellulose, cellulose acetate, cellulose propionate, cellulose butyrate, cellulose acetate butyrate, poly(lactic-co-glycolic acid), poly(lactic acid), poly(ethylene glycol-co-butylene terephthalate) (available as PolyActive® by Octoplus, The Netherlands), and hydrophobic dextran polymer derivatives, and mixtures thereof.

In one embodiment, the poorly aqueous soluble polymer is a hydrophobic dextran polymer derivative comprising an alkyl ester substituent selected from acetate, propionate, butyrate, isobutyrate, and mixtures thereof. In another embodiment, the alkyl ester substituent is selected from acetate and propionate. In yet another embodiment, the alkyl ester substituent is acetate. In another embodiment, the alkyl ester substituent is propionate.

In one embodiment, the degree of substitution of the alkyl ester substituent on the hydrophobic dextran polymer derivative is generally at least 0.5. In another embodiment, the degree of substitution of the alkyl ester substituent is at least 0.75. In still another embodiment, the degree of substitution of the alkyl ester substituent is at least 1.0. In another embodiment, the degree of substitution of the alkyl ester substituent ranges from 0.5 to 2.95. In another embodiment, the degree of substitution of the alkyl ester substituent ranges from 0.5 to 2.0.

The hydrophobic dextran polymer derivatives can be synthesized using procedures outlined in U.S. Patent Publication No. 2012/0003282, the disclosure of which is incorporated herein by reference.

In one embodiment, the mass ratio of the hydrophobic dextran polymer derivative to the cationic dextran polymer derivative ranges from 1:1 to 20:1. In another embodiment, the mass ratio of the hydrophobic dextran polymer derivative to the cationic dextran polymer derivative ranges from 2:1 to 9:1. In another embodiment, the mass ratio of the hydrophobic dextran polymer derivative to the cationic dextran polymer derivative ranges from 3:1 to 6:1.

In one embodiment, the poorly aqueous soluble polymer is biocompatible. In another embodiment, the poorly aqueous soluble polymer is biodegradable.

Compositions

In one embodiment, the composition is in the form of a delivery fluid comprising the active agent and the polymer comprising at least one cationic group. In one embodiment, the fluid comprises (i) a liquid in which both the active agent and polymer comprising at least one cationic group are dissolved therein, (ii) a liquid in which at least a portion of the active agent and at least a portion of the polymer are suspended therein, (iii) a liquid in which at least a portion of the active agent is suspended therein and the polymer is dissolved therein, or (iv) a liquid in which active agent is dissolved therein and the at least a portion of the polymer is suspended therein. In one embodiment, the liquid is selected from water, water for injection (i.e., water for parenteral use, prepared by distillation or reverse osmosis and meeting certain standards for sterility and clarity), isotonic saline, hypertonic saline, and Lactated Ringer's solution. In one embodiment, the delivery fluid further comprises a poorly aqueous soluble polymer.

In another embodiment, the fluid comprises a suspension comprising particles having an average diameter ranging from 10 nm to 10 μm. Individual particles may include the active agent, the polymer comprising at least one cationic group, the poorly aqueous soluble polymer (if present), or any combination thereof. In another embodiment, the fluid comprises a suspension comprising particles having an average diameter ranging from 10 nm to 1 μm. In another embodiment, the fluid comprises a suspension of nanoparticles, the nanoparticles having an average diameter of less than 500 nm. By "nanoparticles" is meant a plurality of small particles in which the average diameter of the particles is less than 500 nm. As used herein, "average diameter" means the effective cumulant diameter as measured by dynamic light scattering (DLS), using for example, Brookhaven Instruments' 90Plus particle sizing instrument. In one embodiment, the nanoparticles have an average diameter of less than 400 nm, less than 300 nm, less than 200 nm, less than 150 nm, less than 100 nm, less than 75 nm, or even less than 50 nm. In another embodiment, the nanoparticles range in diameter from 1 nm to 500 nm, from 1 nm to 400 nm, from 1 nm to 300 nm, from 1 nm to 200 nm, from 10 nm to 400 nm, or from 30 nm to 400 nm.

In another embodiment, the disclosure described herein relates to a dry powder comprising an active agent and a polymer comprising at least one cationic group. In one embodiment, the dry powder comprises particles having an average diameter of less than 500 μm. In another embodiment, the average diameter of the particles is less than 200 μm. In still another embodiment, the average diameter of the particles is less than 100 μm. In one embodiment, the average diameter of the particles ranges from 10 nm to 100 μm. In one embodiment, the average diameter of the particles ranges from 0.5 to 500 μm. In another embodiment, the average diameter of the particles ranges from 0.5 to 200 μm. In one embodiment, the average diameter of the particles ranges from 0.5 to 100 μm. In one embodiment, the average diameter of the particles ranges from 10 to 100 μm. In one embodiment, the average diameter of the particles ranges from 10 to 70 μm. In one embodiment, the average diameter of the particles ranges from 10 to 50 μm. In one embodiment, the average diameter of the particles ranges from 0.5 to 10 μm. In one embodiment, the average diameter of the particles ranges from 0.5 to 7 μm.

In another embodiment, the disclosure described herein relates to a dry powder comprising an active agent and a polymer comprising at least one cationic group that may be reconstituted into a delivery fluid that may be administered intra-articularly. In one embodiment, the dry powder further comprises a poorly aqueous soluble polymer. In one embodiment, the dry powder is reconstituted in a liquid selected from water, water for injection, isotonic saline, hypertonic saline, and Lactated Ringer's solution. In one embodiment, the dry powder, when reconstituted in a liquid forms a delivery fluid comprising a solution of active agent and the polymer comprising at least one cationic group. In another embodiment, the dry powder, when reconstituted in a liquid forms a delivery fluid comprising a suspension, as described herein above.

In one embodiment, the delivery fluid comprises a solution comprising the active agent, and the polymer comprising at least one cationic group. In another embodiment, the delivery fluid further comprises a poorly aqueous soluble polymer. In one embodiment, the delivery fluid comprises particles in suspension having an average diameter ranging from 10 nm to 10 μm.

In one embodiment, the disclosed compositions, when administered to synovial fluid, associate with a component of the synovial fluid. In other words, an intermolecular interaction occurs between at least one component of the composition and at least one component of the synovial fluid. In one embodiment, the polymer comprising at least one cationic group associates with a component of the synovial fluid. In another embodiment, the composition includes a poorly aqueous soluble polymer, and the poorly aqueous soluble polymer associates with a component of the synovial fluid. In yet another embodiment, active agent is joined with the polymer comprising the cationic group and/or the poorly aqueous soluble polymer (if present), and the active agent-polymer complex associates with a component of the synovial fluid.

In one embodiment, the disclosed compositions when administered in vitro to synovial fluid comprising hyaluronate, associate with the hyaluronate present in the synovial fluid. In one embodiment, the compositions form ionic crosslinks with the hyaluronate present in the synovial fluid. In one embodiment, the composition when crosslinked to the hyaluronate forms a gel. As used herein, the term "gel" means a viscous colloid comprising a disperse phase (e.g., synovial fluid) and a continuous phase (e.g., the polymer, or active agent-polymer complex, crosslinked with hyaluronate). In one embodiment, the in vitro synovial fluid has a concentration of hyaluronate of between 1 and 5 mg/mL. In another embodiment, the in vitro synovial fluid has a concentration of hyaluronate of between 3 and 4 mg/mL. In one embodiment, the in vitro synovial fluid consists of distilled water containing hyaluronate. In another embodiment, the in vitro synovial fluid consists of PBS containing hyaluronate. In yet another embodiment, the in vitro synovial fluid is human synovial fluid.

The active agent and polymers (i.e., the polymer comprising at least one cationic group and, if present, the poorly aqueous soluble polymer) are collectively present in the compositions in an amount ranging from 50 wt % to 100 wt %. In one embodiment, the active agent and polymers collectively may constitute at least 60 wt %, or even at least 80 wt % of the composition. In another embodiment, the compositions consist essentially of the active agent and the polymers. By "consist essentially of" is meant that the compositions contains less than 1 wt % of any other excipients and that any such excipients have substantially no effect on the performance and/or properties of the compositions.

The amount of active agent in the compositions may range from 0.01 wt % to 99 wt %. In one embodiment, the amount of active agent in the composition ranges from 0.1 wt % to 80 wt %, or from 0.1 to 60 wt %, or from 1 to 40 wt %. In still another embodiment, the amount of active agent in the composition ranges from 5 wt % to 75 wt %, from 5 wt % to 60 wt %, or from 5 wt % to 50 wt %.

In another embodiment, the active agent is joined with at least one of the polymers present in the composition. When the active agent is joined with the polymer, the active agent may comprise from 0.01 wt % to 99 wt % of the composition. In another embodiment, the amount of active agent joined with the polymer ranges from 0.1 wt % to 90 wt %, from 1 wt % to 80 wt %, from 1 wt % to 60 wt %, or from 1 wt % to 40 wt %.

In one embodiment, the active agent is joined with a poorly aqueous soluble polymer. In another embodiment, the active agent is joined with the polymer comprising at least one cationic group. In still another embodiment, the active agent is joined with both a poorly aqueous soluble polymer and the polymer comprising at least one cationic group.

Methods of Use

In one embodiment, the disclosed compositions are intended for delivery to the intra-articular space injection. In one embodiment, the disclosed compositions, when delivered by intra-articular injection, associate with endogenous hyaluronic acid and/or hyaluronate present in synovial fluids in joints, thereby maintaining the active agent in the intra-articular space and resulting in extended release of the active agent in the joint compared to a composition that does not include a polymer comprising at least one cationic group.

In one embodiment, the disclosed compositions, when administered via intra-articular injection to an in vivo environment containing synovial fluid, form crosslinks, such as ionic crosslinks, with the endogenous hyaluronate and/or hyaluronic acid present in the synovial fluid. In another embodiment, the composition forms an ionically crosslinked gel with endogenous hyaluronate present in the synovial fluid. In some embodiments, formation of a crosslinked gel prolongs local retention of the composition by, for example, reducing convective and/or diffusive transport of the active agent out of the joint. In one embodiment, the in vivo environment is a knee joint.

In one embodiment, a method for delivering an active agent to a joint comprises (a) providing a fluid comprising (i) an active agent, and (ii) a polymer comprising at least one cationic group; and (b) injecting the fluid into an intra-articular space in a human or animal. In another embodiment, the fluid further comprises (iii) a poorly aqueous soluble polymer.

Other features and embodiments of the disclosure will become apparent from the following Examples that are given for illustration rather than for limiting the disclosure's intended scope.

EXAMPLES

Polymers

The following polymers were used in the examples. Poly (ethylacrylate-co-methyl methacrylate-co-trimethylammonioethyl methacrylate chloride), also known as Eudragit® RL100, was obtained from Evonik Industries (Essen, Germany). Other polymers used are given in Table 1.

TABLE 1

| Polymer | Starting Dextran/ Molecular Weight (Daltons) | Alkyl Ester Substituent | Degree of Substitution of the Alkyl Ester Substituent | Ester-Linked Amine-Containing Substituent | Degree of Substitution of the Amine-Containing Substituent |
|---|---|---|---|---|---|
| 1 | Dextran 10,000 | propionate | 1.9 | CH₃-O-C(=O)-CH₂-CH₂-N⁺(CH₃)₂-CH₃ | 0.04 |
| 2 | Dextran 20,000 | acetate | 1.9 | CH₃-O-C(=O)-CH₂-CH₂-N⁺(CH₃)₂-CH₃ | 0.14 |
| 3 | Dextran 10,000 | propionate | 2.4-2.7 | None | 0 |
| 4 | Dextran 10,000 | Propionate Succinate | 1.9 0.23 | None | 0 |
| 5 | Dextran 20,000 | None | 0 | —O-C(=O)-CH₂-CH₂-NH₂ | 0.5 |

Example 1

A nanoparticle formulation consisting of 70 wt % Polymer 3, 25 wt % Polymer 1, and 5 wt % poly(2-methoxy, 5-(2'-ethyl-hexoxy)-1,4-phenylene-vinylene) (MEH-PPV) was made by dissolving 98 mg Polymer 3, 35 mg Polymer 1, and 7 mg MEH-PPV in 7 mL methylene chloride, and mixing this solution with 25 mL milli-Q water using a using a rotor stator (Polytron 3100, Kinematica Inc., Bohemia, N.Y.) at 10,000 rpm for 3 minutes. This coarse emulsion was further emulsified at 12,500 psi for 6 minutes using a Microfluidizer M110S (Microfluidics, Newton, Mass.) fitted with a Z-shaped interaction chamber with a 100-μm-diameter channel. The emulsion was then placed on a rotoevaporator, where the methylene chloride was removed under reduced pressure at approximately 25° C. The resulting aqueous suspension was filtered through a 1-μm glass-microfiber syringe filter. Gravimetric measurement showed a final concentration of 3.9 mg/mL nanoparticles in aqueous solution.

Nanoparticle size was measured by dynamic light scattering (DLS) using a BI-200SM nanoparticle size analyzer with a BI-9000AT correlator (Brookhaven Instruments Corp., Long Island, N.Y.). Nanoparticle size is reported as the effective hydrodynamic diameter determined using the cumulant cubic algorithm. The mean diameter was found to be 177 nm.

Association with Human Synovial Fluid

The nanoparticles of Example 1 were examined to determine if the particles associated with hyaluronate present in human synovial fluid in an in vitro test. This test was performed by mixing 0.5 mL of the aqueous nanoparticle solution of Example 1 (3.9 mg/mL) with 1 mL human synovial fluid (isolated from osteoarthritis patients, part #HYSYNOV-OA, Bioreclamation, Inc., Hicksville, N.Y.). Association was observed.

Optical Micrographs of Associations

To further examine the association of nanoparticles with synovial fluid in vitro, optical micrographs were taken immediately upon mixing. For this test, nanoparticles were formed using Polymer 2 (containing a fluorescence imaging dye) as follows. First, 30 mg Polymer 2 was dissolved in 0.5 mL methanol by vortexing for 15 minutes. This solution was injected into 5 mL water stirred at 60 rpm to precipitate nanoparticles. The solvent was removed using a rotoevaporator.

The nanoparticle solution was mixed in vitro with human synovial fluid and fluorescence microscopy was used to obtain the image shown in FIG. 1. Immediately upon mixing, an extended fibrous fluorescent material was formed.

Examples 2 and 3

An RFK peptide (Arg-Phe-Lys) labeled with fluorescein isothiocyanate (RFK-FITC), which may be obtained from American Peptide Company, Inc. (Sunnyvale, Calif.), may be used in these examples. The active agent may first be attached to Polymer 4 using the following procedure. First, 192 mg of Polymer 4 may be mixed with 500 mg RFK-FITC, 42 mg 1-ethyl-3-(3-dimethylaminopropyl) carbodiimide (EDCI), and 17 mg 4-dimethyl aminopyridine (DMAP) and added to 6 mL dimethylsulfoxide (DMSO). The resulting polymer with the active agent covalently bound thereto, may then be precipitated in water, and purified by washing with water or using dialysis to remove unreacted materials.

To form nanoparticles of Example 2, 75 wt % of the active-containing polymer and 25 wt % of Polymer 1 may be dissolved in a water-miscible solvent, such as methanol, tetrahydrofuran (THF), or the like. The resulting solution can then be injected into water at a volume ratio (water:organic) of 2:1 to 15:1 or higher (e.g., more water) to form nanoparticles. The organic solvent can then be removed by evaporation, spray drying, extraction, diafiltration, pervaporation, vapor permeation, distillation, and filtration. The nanoparticle size may then be measured by DLS as previously described.

To form nanoparticles of Example 3, 85 wt % of the active-containing polymer and 15 wt % of Polymer 1 may be dissolved in a water-miscible solvent, as described for Example 2. The resulting solution can then be injected into water at a volume ratio (water:organic) of 2:1 to 15:1 or higher to form nanoparticles. The organic solvent can then be removed as described for Example 2, and the nanoparticle size measured by DLS.

Example 4

This example demonstrates the use of a caspase inhibitor as the active agent. A caspase inhibitor, such as Z-VAD-FMK, may be obtained from EMD Millipore, Billerica, Mass. This active may be covalently bound to Polymer 4 using a procedure similar to that described for Examples 2 and 3.

To form nanoparticles of Example 4, 75 wt % of the caspase inhibitor containing polymer and 25 wt % of Polymer 1 may be dissolved in a water-miscible solvent, such as methanol, tetrahydrofuran (THF), or the like. The resulting solution can then be injected into water at a volume ratio (water:organic) of 2:1 to 15:1 or higher to form nanoparticles. The organic solvent can then be removed by evaporation, spray drying, extraction, diafiltration, pervaporation, vapor permeation, distillation, and filtration. The nanoparticle size may then be measured by DLS as previously described.

Example 5

A caspase inhibitor may be covalently bound to Polymer 5 using a procedure similar to that described for Examples 2 and 3. To form nanoparticles of Example 5, the caspase inhibitor containing polymer may be dissolved in a water miscible solvent, such as methanol, tetrahydrofuran (THF), or the like. The resulting solution can then be injected into water at a volume ratio (water:organic) of 2:1 to 15:1 or higher to form nanoparticles. The organic solvent can then be removed by evaporation, spray drying, extraction, diafiltration, pervaporation, vapor permeation, distillation, and filtration. The nanoparticle size may then be measured by DLS as previously described.

Example 6

A nanoparticle formulation consisting of 75 wt % Polymer 3, 20 wt % Eudragit® RL100, and 5 wt % MEH PPV was prepared for fluorescent imaging by dissolving 37.5 mg of Polymer 3 and 12.5 mg of Eudragit® RL100 in 5 mL of tetrahydrofuran (THF), in which 2.5 mg of MEH PPV was dissolved. This solution was injected into 50 mL of water. The solution was rotoevaporated to remove THF, leaving 8 mL of suspension. The suspension was then filtered through a 1 µm syringe filter before use. The resulting suspension contained nanoparticles. When added in vitro to human synovial fluid, association was observed.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A composition comprising:
    a dry powder, comprising
        (a) an active agent suitable for injection into an intra-articular space, the active agent comprising an anti-inflammatory, an antibiotic, an autoimmune disorder agent, an antiviral agent, an anticlotting agent, an antifungal agent, a corticosteroid, a caspase inhibitor, an aggrecanase inhibitor, a matrix metalloproteinase inhibitor, a disease-modifying anti-rheumatic drug, a disease-modifying osteoarthritis drug, an analgesic, or any combination thereof, and
        (b) a polymer comprising at least one cationic group, selected from a cationic dextran polymer derivative comprising an ester-linked amine-containing substituent selected from

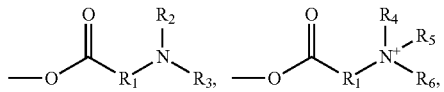

and mixtures thereof, wherein Ri is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03,
wherein the dry powder, when admixed with a liquid and injected into an intra-articular space, maintains the active agent in the intra-articular space by associating with endogenous material in the intra-articular space.

2. The composition of claim 1, further comprising:
    a poorly aqueous soluble polymer.

3. The composition of claim 1 wherein, after administration to an in vitro synovial fluid, at least one of said active agent and said polymer is associated with at least one component of said synovial fluid.

4. The composition of claim 1, further comprising a liquid, wherein said dry powder, when admixed with the liquid, forms a fluid suitable for injecting into an intra-articular space of a human or animal, wherein, after injection, at least one of said active agent and said polymer is associated with endogenous material in the intra-articular space.

5. The composition of claim 4 wherein said fluid is a solution of said active agent and said polymer comprising at least one cationic group.

6. The composition of claim 4 wherein said fluid comprises a suspension of said active agent and said polymer comprising at least one cationic group.

7. The composition of claim 1 wherein said cationic dextran polymer derivative further comprises an alkyl ester substituent, selected from acetate, propionate, and mixtures thereof, wherein the degree of substitution of said alkyl ester substituent is at least 0.05.

8. The composition of claim 2, wherein said poorly aqueous soluble polymer is a hydrophobic dextran polymer derivative comprising an alkyl ester substituent selected from acetate, propionate, butyrate, isobutyrate, and mixtures thereof, wherein the degree of substitution of the alkyl ester substituent is at least 0.05.

9. The composition of claim 1 wherein said active agent is joined to said cationic dextran polymer derivative.

10. The composition of claim 9 wherein said active agent is joined covalently or non-covalently to said cationic dextran polymer derivative.

11. The composition of claim 10 wherein said active agent is joined to said dextran polymer derivative using a physiologically labile covalent linkage.

12. The composition of claim 2 wherein said active agent is joined to said poorly aqueous soluble polymer.

13. The composition of claim 12 wherein said active agent is joined covalently or non-covalently to said poorly aqueous soluble polymer.

14. The composition of claim 13 wherein said active agent is joined to said poorly aqueous soluble polymer using a physiologically labile covalent linkage.

15. A method for maintaining an active agent in an intra-articular space, comprising:
(a) providing a composition comprising a dry powder, comprising (i) an active agent suitable for injection into an intra-articular space, the active agent comprising an anti-inflammatory, an antibiotic, an autoimmune disorder agent, an antiviral agent, an anticlotting agent, an antifungal agent, a corticosteroid, a caspase inhibitor, an aggrecanase inhibitor, a matrix metalloproteinase inhibitor, a disease-modifying anti-rheumatic drug, a disease-modifying osteoarthritis drug, an analgesic, or any combination thereof, and (ii) a polymer comprising at least one cationic group, selected from a cationic dextran polymer derivative comprising an ester-linked amine-containing substituent selected from

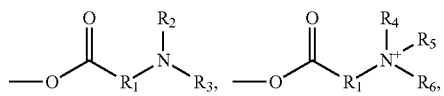

and mixtures thereof, wherein $R_1$ is selected from $C_1$, $C_2$, $C_3$, or $C_4$ alkyl groups, $R_2$ and $R_3$ may be the same or different and are selected from hydrogen, methyl and ethyl groups, and $R_4$, $R_5$, and $R_6$ may be the same or different and are selected from methyl and ethyl groups, and wherein the degree of substitution of said ester-linked amine-containing substituent is at least 0.03; and
(b) admixing the composition with a liquid to form a fluid, thereby forming a mixture capable of associating with endogenous material in the intra-articular space.

16. The method of claim 15 wherein said fluid further comprises a poorly aqueous soluble polymer.

17. The method of claim 15 wherein said fluid comprises a solution in which said active agent and said polymer comprising at least one cationic group are dissolved.

18. The method of claim 15 wherein said fluid comprises a suspension of particles.

19. The method of claim 18 wherein said fluid comprises a suspension of nanoparticles.

20. The method of claim 15 wherein said active agent is joined with said polymer comprising at least one cationic group.

21. The method of claim 16 wherein said active agent is joined with said poorly aqueous soluble polymer.

22. The method of claim 15 wherein said cationic dextran polymer derivative further comprises an alkyl ester substituent selected from acetate, propionate, butyrate, isobutyrate, and mixtures thereof, wherein the degree of substitution of said alkyl ester substituent is at least 0.05.

23. The method of claim 16 wherein said poorly aqueous soluble polymer is selected from ethylcellulose, cellulose acetate, cellulose propionate, cellulose butyrate, cellulose acetate butyrate, poly(lactic-co-glycolic acid), poly(lactic acid), poly(ethylene glycol-co-butylene terephthalate), hydrophobic dextran polymer derivatives, and mixtures thereof.

24. The method of claim 23 wherein said poorly aqueous soluble polymer is a hydrophobic dextran polymer derivative comprising an alkyl ester substituent selected from acetate, propionate, butyrate, isobutyrate, and mixtures thereof, wherein the degree of substitution of the alkyl ester substituent is at least 0.05.

* * * * *

UNITED STATES PATENT AND TRADEMARK OFFICE
CERTIFICATE OF CORRECTION

PATENT NO.         : 9,084,727 B2
APPLICATION NO.    : 13/468965
DATED              : July 21, 2015
INVENTOR(S)        : Michael M. Morgen et al.

Page 1 of 1

It is certified that error appears in the above-identified patent and that said Letters Patent is hereby corrected as shown below:

In the Claims:

Column 16, line 12, "Ri" should be --$R_1$--

Signed and Sealed this
Ninth Day of August, 2016

Michelle K. Lee
*Director of the United States Patent and Trademark Office*